United States Patent
Zeng et al.

(10) Patent No.: US 9,067,965 B2
(45) Date of Patent: Jun. 30, 2015

(54) PREPARATION METHOD OF ROCURONIUM

(75) Inventors: Zhiwen Zeng, Zhejiang (CN); Wenling Zhang, Zhejiang (CN); Peng Wang, Zhejiang (CN); Xini Zhang, Zhejiang (CN)

(73) Assignee: Zhejiang Huahai Pharmaceutical Co., Ltd., Zhejiang (CN)

( * ) Notice: Subject to any disclaimer, the term of this patent is extended or adjusted under 35 U.S.C. 154(b) by 0 days.

(21) Appl. No.: 13/991,316

(22) PCT Filed: Jan. 26, 2011

(86) PCT No.: PCT/CN2011/070617
§ 371 (c)(1),
(2), (4) Date: Jun. 3, 2013

(87) PCT Pub. No.: WO2012/100411
PCT Pub. Date: Aug. 2, 2012

(65) Prior Publication Data
US 2013/0303753 A1    Nov. 14, 2013

(51) Int. Cl.
*C07J 43/00* (2006.01)

(52) U.S. Cl.
CPC .................................... *C07J 43/003* (2013.01)

(58) Field of Classification Search
CPC ...................................................... C07J 43/003
USPC ........................................................ 540/96
See application file for complete search history.

(56) References Cited

U.S. PATENT DOCUMENTS

| | | |
|---|---|---|
| 4,894,369 A | 1/1990 | Sleigh et al. |
| 7,579,461 B2 | 8/2009 | Adar et al. |
| 7,642,246 B2 | 1/2010 | Mendez et al. |
| 2006/0009485 A1 | 1/2006 | Friedman et al. |

FOREIGN PATENT DOCUMENTS

| | | |
|---|---|---|
| CN | 101323636 A | 12/2008 |
| CN | 101381390 A | 3/2009 |
| EP | 0 287 150 A | 10/1988 |
| KR | 20100063370 A | 6/2010 |
| WO | WO 2007033348 A2 | 3/2007 |
| WO | WO 2010118699 A1 | 10/2010 |

OTHER PUBLICATIONS

International Search Report dated Nov. 3, 2011 from corresponding International Application No. PCT/CN2011/070617.
Extended European Search Report dated Nov. 26, 2014 from corresponding European Application No. 11856787.
Database WPI Week 201075 Thomson Scientific, London, GB; AN 2010-N23577 XP002725380, & WO 2010/118699 A1 (Chongqing Pharm Res Inst Co Ltd) Oct. 21, 2010, 4 pages.
Platzer N et al: Easy Alkylation of Purine Bases by Solid-Liquid Phase Transfer Catalysis Without Solvent, Tetrahedron, Elsevier Science Publishers, Amsterdam, NL, vol. 43, No. 9, Jan. 1, 1987, pp. 2101-2108, XP026596461, ISSN: 0040-4020, DOI: 10.1016/S0040-4020(01)86791-0.

*Primary Examiner* — Brenda Coleman
(74) *Attorney, Agent, or Firm* — Wolf, Greenfield & Sacks, P.C.

(57) ABSTRACT

A method for preparing rocuronium is disclosed. 2β-(4-Morpholinyl)-16β-(1-pyrrolidinyl)-5α-androstan-3α-ol-17β-acetate is used as a starting material and is directly reacted with 3-bromopropene at ambient temperature to produce rocuronium.

13 Claims, 1 Drawing Sheet

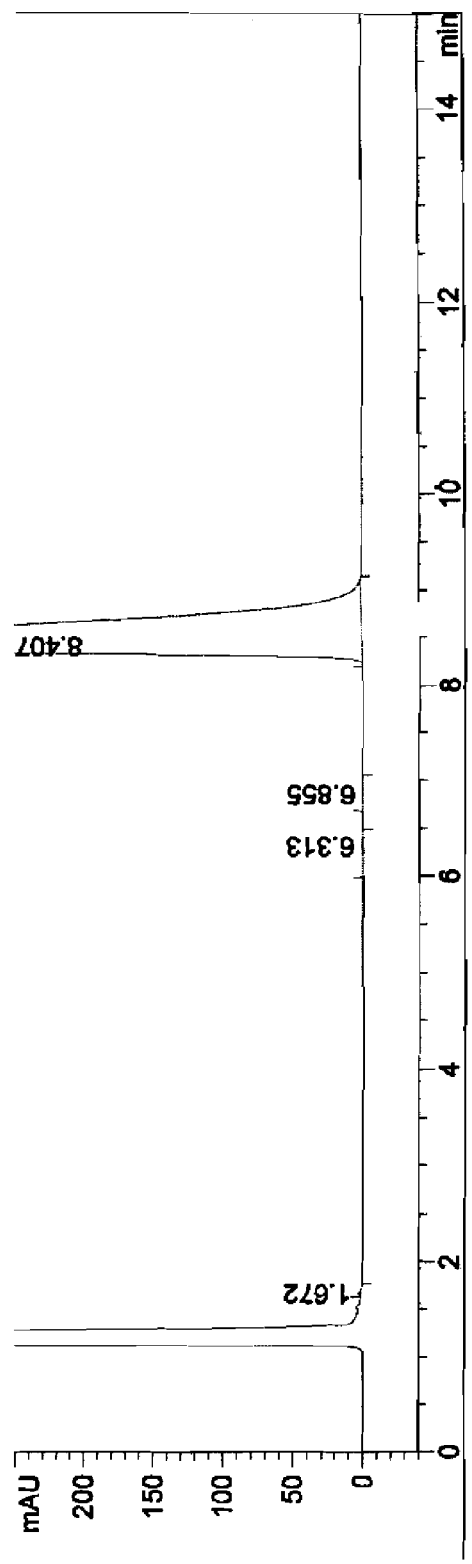

PREPARATION METHOD OF ROCURONIUM

RELATED APPLICATIONS

This application is a national stage filing under 35 U.S.C. §371 of International Application No. PCT/CN2011/070617, filed Jan. 26, 2011, the entirety of which is incorporated herein by reference.

FIELD OF THE INVENTION

The present invention relates to the field of medicinal chemistry, and specifically relates to a method for preparing rocuronium bromide which is a steroidal muscle relaxant.

BACKGROUND OF THE INVENTION

Rocuronium bromide is a novel mono-quaternary ammonium muscle relaxant and is used as an anesthetic adjuvant drug for tracheal intubation during anesthetization and muscle relaxation in surgical operation. Rocuronium bromide is a non-depolarizing muscle relaxant used clinically with the most rapid onset. The characteristics thereof include rapid onset, rapid recovery, weak inhibitory effects on cardiovascular system, and no histamine releasing effects. This drug is the most widely used muscle relaxant internationally, and is the first-ranked muscle relaxant in consumption used in North America and most European countries. The chemical formula thereof is as follows:

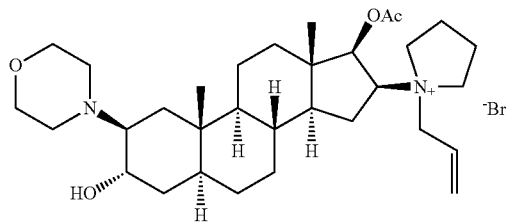

European patent EP 0287150 initially discloses the preparation method and use thereof, in which 2β-(4-morpholinyl)-16β-(1-pyrrolidinyl)-5α-androstan-3α-ol-17β-acetate is reacted with 3-bromopropene in dichloromethane for 22 h, wherein the molar volume ratio of the three materials is 1 mol:8.2 mol:10 L. Separation by column chromatography obtained the target product. This method has certain disadvantages: high equivalent amount of 3-bromopropene is applied; the reaction time is long; the treatment needs column separation, which is not conducive to practical productions. U.S. Pat. No. 7,579,461 involves reacting 2β-(4-morpholinyl)-16β-(1-pyrrolidinyl)-5α-androstan-3α-ol-17β-acetate with bromopropene in acetone under reflux to react for 10 h, wherein the molar volume ratio of the three materials is 1 mol:2.3 mol:5 L, removing the solvent under reduced pressure to give rocuronium bromide. Although less equivalent amount of 3-bromopropene is applied in this method, the reaction process requires heating under reflux and longer reaction time. Rocuronium bromide is poor in thermal stability, which results in large amount of impurities in the reaction. The method described in U.S. Pat. No. 7,642,246 is that 2β-(4-morpholinyl)-16β-(1-pyrrolidinyl)-5α-androstan-3α-ol-17β-acetate is reacted with bromopropene and solid powder of sodium carbonate in dichloromethane under the protection of nitrogen gas for 24 h, wherein molar volume ratio of the four materials is 1 mol:2 mol:4.6 mol:2.3 L. In this method, since it is the two-phase reaction, and has a long reaction time and a low conversion ratio. Chinese patent CN 101323636 discloses that 2β-(4-morpholinyl)-16β-(1-pyrrolidinyl)-5α-androstan-3α-ol-17β-acetate is reacted with bromopropene in ethyl ether at ambient temperature for 2 days, wherein the molar volume ratio of the three materials is 1 mol:5.6 mol:9.8 L, and when the reaction is completed, half of the solvent is removed under reduced pressure, and the residue is recrystallized from acetone to give the target product. Also, reaction time of this method is too long to be conducive to industrialized production.

It can be seen from the methods reported by currently published literatures for technical information that in quaterisation reactions, large amount of solvent and 3-bromopropene are generally required to be added to perform such reactions, and the reaction time is quite long and the after-treatment is cumbersome, and thus they are not conducive to industrialized production. In addition, 3-bromopropene is a potentially genotoxic substance, which will lead to excessive residue in final products if it is employed in large amount in the reaction. The present invention provides a method for reducing the application amount of 3-bromopropene and the reaction time, while ensuring the yield and purity of rocuronium bromide, so as to further improve the production efficiency, reduce the production cost, and simplify the operation. According to the method of the present patent, the residue of 3-bromopropene in rocuronium bromide can be controlled below 10 ppm.

SUMMARY OF THE INVENTION

The object of the present invention is to improve existing preparation methods and provide a novel method for preparing rocuronium bromide, which can overcome the above disadvantages in the prior art.

The inventors have found the following phenomena through studies, and creative improvements have been made:

First, 2β-(4-morpholinyl)-16β-(1-pyrrolidinyl)-5α-androstan-3α-ol-17β-acetate (hereinafter referred to as "the acetate") can be well dissolved in 3-bromopropene, even if wetted by 3-bromopropene without a solvent under a protection of nitrogen, the acetate can still be rapidly changed into a quaternized salt. However, the product rocuronium bromide is insoluble in 3-bromopropene, it is precipitated once formed. Based on the above phenomena, 3-bromopropene is a good solvent itself, thus it is not necessary to add other solvents in the reaction. Further more, the product is immediately precipitated once formed, which enables the reaction equilibrium to move in the forward direction.

Second, 3-bromopropene has potential genotoxicity, and is extremely detrimental when it enters into human body in large amount, thus the employment of 3-bromopropene should be controlled as strictly as possible. However, in terms of the reaction itself, reactant molecules in the system without addition of a solvent are easier to "collide and contact" with each other to make the reaction more rapid and complete. The amount of unreacted starting materials (i.e. Impurity A having the following formula) can be reduced by effectively controlling the reaction time. Thus, the application amount of 3-bromopropene can be greatly reduced without a solvent, and the reaction time will also be shortened and the reaction will be quite complete.

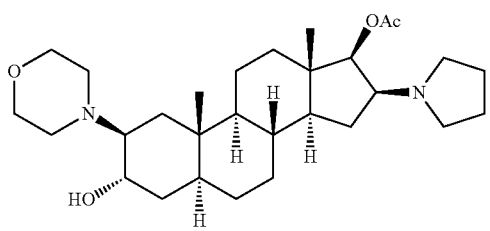

Impurity A

Third, the product needs to be crystallized once again in order to control the quality of the product. This object can be achieved by directly adding small amount of good solvent for rocuronium bromide into the reaction solution after the reaction is completed, and mixing, to dissolve the product, which is then added dropwise into an anti-solvent for rocuronium bromide. In comparison with the prior art, the amount of solvent employed is greatly reduced, and the operation is also quite convenient.

Based on the methods reported by currently published literatures for technical information, the following rational improvements have been made in the present invention: on the promise of ensuring the yield and the purity of rocuronium bromide, the present invention do not require adding reaction solvent, and can effectively control the residue amount of 3-bromopropene in the product while ensuring the shortest reaction time and the lowest application amount of 3-bromopropene.

The specific embodiment of the present invention is as follows:

1. the acetate is used as a starting material, and is directly reacted with 3-bromopropene.

Wherein the molar amount of 3-bromopropene is 2~10 equivalent amount of the acetate, and preferably 3~6 equivalent amount. The reaction temperature is 0~40° C., and preferably 10~25° C. The reaction can be completed within 5 h, and preferably the reaction time is 1~1.5 h.

2. A good solvent is added to dissolve the reactants after the reaction is completed.

Wherein the amount of good solvent added is 1~2.5 L/mol equivalent amount of the volume molar ratio of the acetate (the unit of volume molar ratio used below is L/mol), and preferably 1~2 equivalent amount. The good solvent employed can be acetonitrile, dichloromethane, acetone, or a mixture thereof, wherein the preferred solvent is acetonitrile or dichloromethane.

3. The reaction solution is added dropwise into an anti-solvent and stirred for the crystallization.

The anti-solvent employed can be ethyl ether, methyl tert-butyl ether, isopropyl ether, isobutyl acetate, or a mixture thereof, wherein the preferred solvent is methyl tert-butyl ether or isobutyl acetate.

4. The filter cake is collected after filtration, and the finished product of rocuronium bromide is obtained after freeze-drying processing.

Reaction equation:

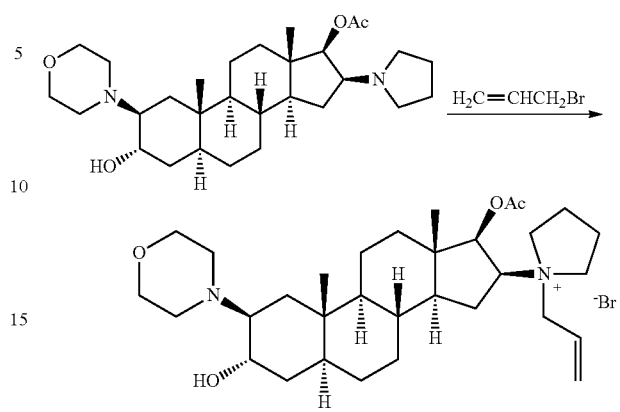

In the method for preparing rocuronium bromide according to the present invention, 2β-(4-morpholinyl)-16β-(1-pyrrolidinyl)-5α-androstan-3α-ol-17β-acetate is used as a starting material, and is directly reacted with 3-bromopropene. After the reaction is completed, dissolving the reaction mixture in a good solvent, and adding an anti-solvent into the solution to crystallize the solid, then rocuronium bromide product is obtained by filtration.

The application of the above method in pharmaceutical chemical production. In comparison with the prior art for preparing rocuronium bromide, the preparation of rocuronium bromide according to the present invention can effectively reduce the application amount of 3-bromopropene, the reaction time is short, the process is concise, the operation is simple, and it is easily controllable, thus it is quite conducive to industrialized production. The HPLC purity of the obtained rocuronium bromide can be up to 99%, and the yield of the product reaches about 98%, while the HPLC purity of Impurity A is less than 0.1%, and the content of 3-bromopropene is less than 10 ppm.

DESCRIPTION OF THE DRAWINGS

FIG. 1 is the HPLC chromatogram of the product prepared by the method of the present invention.

DETAILED EMBODIMENTS

The followings are examples of the present patent, however, the protection scope of the present invention is not limited to them.

Example 1

The acetate 100.0 g and 3-bromopropene 36 mL were added into a 250 mL flask under the protection of nitrogen gas, and reacted at 5° C. for 3 h. After the reaction was completed, acetonitrile 205 mL was added and stirred to dissolve the solid. The solution was slowly added dropwise into 16.5 L methyl tert-butyl ether, and then stirred in ice bath for 1 h. The filter cake was collected by filtration, freeze-dried to obtain 118.5 g of a white solid. USP method was employed to detect, and the HPLC purity of rocuronium bromide was 99.5% with Impurity A≤LOQ (0.05%), and the chromatogram is shown in FIG. 1.

The content of 3-bromopropene was detected by HPLC with the following chromatographic conditions:

Instrument: high performance liquid chromatographic instrument

Liquid chromatographic column: shimpack C18 150×6.0 mm, 5 μm

Mobile phase: water:acetonitrile=40:60

Column temperature: 30° C. Detection wavelength: 210 nm

Flow rate: 1.0 mL/min Sample size: 10 μL

Running time: 20 min

2 Preparation of the Solutions

Diluent: acetonitrile:water=60:40 (% V/V)

Blank solution: diluent

Standard solution: 40 mL standard substance of 3-bromopropene was weighed, and was precisely weighed in a 20 mL volumetric flask, dissolved with the diluent and diluted to the scale mark; 10.0 mL of the solution was accurately pipetted to a 100 mL volumetric flask, diluted to the scale mark with the diluent, and then 10.0 mL of the solution was accurately pipetted to a 100 mL volumetric flask, diluted to the scale mark with the diluent, and mixed.

Test solution: 200 mg test substance was weighed, and was precisely weighed in a 20 mL volumetric flask, dissolved with the diluent and diluted to the scale mark, and the test result showed that the residue amount of 3-bromopropene was 6 ppm.

Example 2

The acetate 100.0 g and 3-bromopropene 70 mL were under the protection of nitrogen gas in a 250 mL flask and controlled at 20° C. to react for 1.25 h to complete. Acetonitrile 400 mL was added and stirred to dissolve the solid. The filtrate was slowly added dropwise into 24 L methyl tert-butyl ether, and then stirred in ice bath for 1 h, filtered to collect the filter cake, which was freeze-dried to give 122.0 g white solid. USP method was employed to detect, the HPLC purity of rocuronium bromide was 99.5% with Impurity A≤LOQ (0.05%), and the residue amount of 3-bromopropene was detected to be 6 ppm by HPLC.

Example 3

The acetate 100.0 g and 3-bromopropene 70 mL were under the protection of nitrogen gas in a 250 mL flask and reacted at 30° C. for 1.25 h. After the reaction was completed, dichloromethane 205 mL was added and stirred to dissolve the solid. The solution was slowly added dropwise into 20 L of ethyl ether, and then stirred in ice bath for 1 h, filtered to collect the filter cake, which was freeze-dried to give 117.3 g white solid. USP method was employed to detect, the HPLC purity of rocuronium bromide was 99.5% with Impurity A≤LOQ (0.05%), and the residue amount of 3-bromopropene was detected to be 6 ppm by HPLC.

Example 4

The acetate 100.0 g and 3-bromopropene 106 mL were under the protection of nitrogen gas in a 250 mL flask and reacted at 20° C. for 1.25 h. After the reaction was completed, acetone 205 mL was added and stirred to dissolve the solid. The solution was slowly added dropwise to 20 L of isopropyl ether, and then stirred in ice bath for 1 h, filtered to collect the filter cake, which was freeze-dried to give 118.3 g of a white solid. USP method was employed to detect, the HPLC purity of rocuronium bromide was 99.5% with Impurity A≤LOQ (0.05%), and the residue amount of 3-bromopropene was detected to be 5 ppm by HPLC.

The method for preparing rocuronium bromide provided by the present invention has been described by the examples, and a skilled in the art can obviously achieve the present invention by changing or appropriately modifying and combining the preparation method without departing from the content, spirit and scope of the present invention. Specifically, all the similar replacements and changes are obvious to a skilled in the art, and they are all deemed to be within the spirit, scope and content of the present invention.

The invention claimed is:

1. A method for preparing rocuronium bromide, wherein 2β-(4-morpholinyl)-16β-(1-pyrrolidinyl)-5α-androstan-3α-ol-17β-acetate is reacted with 3-bromopropene without a solvent; after the reaction is completed, the reaction mixture is dissolved in a solvent, and an anti-solvent is added; rocuronium bromide product is obtained by filtration,

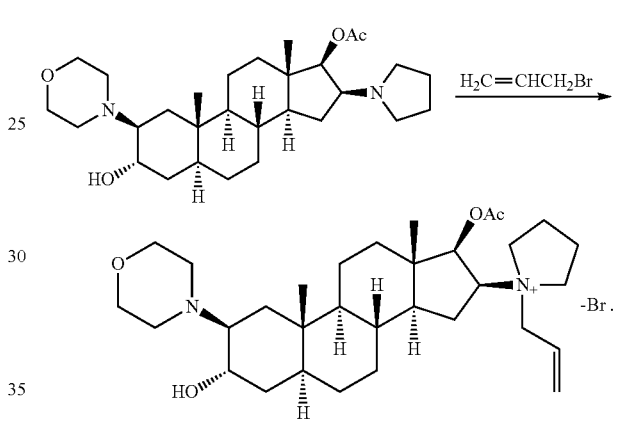

2. The method according to claim 1, wherein the molar amount of 3-bromopropene is 2 to 10 equivalent of the acetate.

3. The method according to claim 1, wherein the reaction temperature is 0 to 40° C.

4. The method according to claim 3, wherein the reaction temperature is 10 to 25° C.

5. The method according to claim 1, wherein the solvent is acetonitrile, dichloromethane, acetone, or a mixture thereof.

6. The method according to claim 1, wherein the anti-solvent is ethyl ether, methyl tert-butyl ether, isopropyl ether, isobutyl acetate, or a mixture thereof.

7. The method according to claim 2, wherein the molar amount of 3-bromopropene is 3-6 equivalent of the acetate.

8. The method according to claim 1, wherein the solvent is 1~2.5 L/mol of the acetate.

9. The method according to claim 8, wherein the solvent is 1~2 L/mol of the acetate.

10. The method according to claim 5, wherein the solvent is acetonitrile or dichloromethane.

11. The method according to claim 6, wherein the anti-solvent is methyl tert-butyl ether or isobutyl acetate.

12. The method according to claim 1, wherein the solvent is dichloromethane, and the anti-solvent is ethyl ether.

13. The method according to claim 1, wherein the solvent is acetone, and the anti-solvent is isopropyl ether.

* * * * *